(12) United States Patent
Huang et al.

(10) Patent No.: US 10,980,766 B2
(45) Date of Patent: Apr. 20, 2021

(54) ENTACAPONE-RELATED COMPOUNDS TO TREAT MACULAR DEGENERATION

(71) Applicant: National Institute of Biological Sciences, Beijing, Beijing (CN)

(72) Inventors: Niu Huang, Beijing (CN); Shiming Peng, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 0 days.

(21) Appl. No.: 16/283,117

(22) Filed: Feb. 22, 2019

(65) Prior Publication Data

US 2019/0183842 A1   Jun. 20, 2019

Related U.S. Application Data

(63) Continuation of application No. PCT/CN2017/098575, filed on Aug. 23, 2017.

(30) Foreign Application Priority Data

Aug. 24, 2016 (WO) ............... PCT/CN2016/096472

(51) Int. Cl.
| | |
|---|---|
| *A61K 31/277* | (2006.01) |
| *A61P 27/02* | (2006.01) |
| *A61K 9/00* | (2006.01) |
| *A61K 45/06* | (2006.01) |
| *A61K 31/397* | (2006.01) |
| *A61K 31/426* | (2006.01) |
| *A61K 31/428* | (2006.01) |
| *A61K 31/433* | (2006.01) |
| *A61K 31/4402* | (2006.01) |
| *A61K 31/4453* | (2006.01) |
| *A61K 31/4965* | (2006.01) |
| *A61K 31/505* | (2006.01) |
| *A61K 31/535* | (2006.01) |

(52) U.S. Cl.
CPC .......... *A61K 31/277* (2013.01); *A61K 9/0051* (2013.01); *A61K 45/06* (2013.01); *A61P 27/02* (2018.01); *A61K 31/397* (2013.01); *A61K 31/426* (2013.01); *A61K 31/428* (2013.01); *A61K 31/433* (2013.01); *A61K 31/4402* (2013.01); *A61K 31/4453* (2013.01); *A61K 31/4965* (2013.01); *A61K 31/505* (2013.01); *A61K 31/535* (2013.01)

(58) Field of Classification Search
CPC combination set(s) only.
See application file for complete search history.

(56) References Cited

U.S. PATENT DOCUMENTS

| | | | |
|---|---|---|---|
| 5,112,861 | A | 5/1992 | Backström et al. |
| 10,301,264 | B2 | 5/2019 | Harper et al. |
| 2010/0190851 | A1 | 7/2010 | Kranich et al. |
| 2014/0148383 | A1 | 5/2014 | Huang et al. |
| 2015/0031655 | A1 | 1/2015 | Ghribi |
| 2016/0222001 | A1* | 8/2016 | Barrow ................. A61P 25/18 |
| 2016/0222011 | A1* | 8/2016 | Barrow ............... C07D 215/36 |

FOREIGN PATENT DOCUMENTS

| | | |
|---|---|---|
| EP | 1946756 A1 | 7/2008 |
| JP | 2016-504270 A | 2/2016 |
| WO | WO 2007/018943 A2 | 2/2007 |
| WO | WO 2007/144169 A2 | 12/2007 |
| WO | 2007/018943 A1 | 10/2008 |
| WO | WO 2009/003226 A1 | 1/2009 |
| WO | WO 2010/022140 A1 | 2/2010 |
| WO | WO 2015/095257 A2 | 6/2015 |
| WO | WO 2016/206573 A1 | 12/2016 |

OTHER PUBLICATIONS

State Intellectual Property Office of the P.R. China, International Search Report issued in International Patent Application No. PCT/CN2017/098575 (dated Nov. 28, 2017).
Yonekawa et al., "Clinical Characteristics and Current Treatment of Age-Related Macular Degeneration," *Cold Spring Harbor Perspectives in Medicine*, 5(1): 1-18 (2014).
European Patent Office, Extended European Search Report issued in European Patent Application No. 17842920.5 (dated Mar. 17, 2020).
Australian Government IP Australia, Examination Report in Australian Patent Application No. 2017317129 (dated Jun. 18, 2019).
Japanese Patent Office, Notice of Reasons for Refusal issued in Japanese Patent Application No. 2019-510788 (dated Mar. 3, 2020).

* cited by examiner

*Primary Examiner* — Kortney L. Klinkel
*Assistant Examiner* — Tori Strong
(74) *Attorney, Agent, or Firm* — Green, Griffith & Borg-Breen LLP

(57) ABSTRACT

The invention provides use of entacapone, an entacapone derivative or a stereoisomer, hydride, or pharmaceutically-acceptable salt thereof, in a person in need thereof, to treat or inhibit macular degeneration or age-related macular degeneration, and related compostions.

4 Claims, 1 Drawing Sheet

ENTACAPONE-RELATED COMPOUNDS TO TREAT MACULAR DEGENERATION

CROSS-REFERENCE TO RELATED APPLICATIONS

This application is a continuation of co-pending International Patent Application No. PCT/CN2017/098575 tiled on Aug. 23, 2017, and claims the benefit of International Patent Application No. PCT/CN2016/096472 filed on Aug. 24, 2016, the disclosures of which are incorporated by reference in their entireties herein.

INTRODUCTION

Macular degeneration is a disease which can lead to loss of central vision due to damage in macula of the retina. It affects millions of people globally, and typically occurs in older people (so-called age-related macular degeneration, AMD). Genetic factors may play a role in this disease, as well as lifestyle: smoking, exposure to sunlight and unhealthy energy intake are the common risk factors. In 2010, there were 23.5 million patients globally, and it is the fourth most common cause of blindness after cataracts, preterm birth, and glaucoma. In the United States, AMD is the most common cause of vision loss in people over the age of fifty. See, e.g. Mehta, S., Age-Related Macular Degeneration. Prim Care 2015, 42 (3), 377-91; Velez-Montoya, et al., Current knowledge and trends in age-related macular degeneration: genetics, epidemiology, and prevention. Retina 2014, 34 (3), 423-41. There is no cure or AMD, though it is treated with laser coagulation, and more commonly with drugs that inhibit the growth of blood vessels, e.g. de Jong P T (2006). "Age-related macular degeneration". N Engl J Med. 355 (14): 1474-1485.

We previously disclosed in US2014/0148383A1 identification of a known FDA approved drug—entacapone ((2E)-2-cyano-3-(3,4-dihydroxy-5-nitrophenyl)-N,N-diethylprop-2-enamide), as an FTO inhibitor using structure-based virtual screening method in combination with biological activity measurements, including enzymatic activity, cellular activity and in high-fat diet induced obesity (DIO) animal model. We also previously disclosed in PCT/CN2015/082052 derivatives of entacapone having related activities.

Entacapone is a catechol-O-methyltransferase (COMT) inhibitor used for treating Parkinson disease, typically administered in conjunction with dopamine derivatives levodopa (L-DOPA) or carbidopa, see Comtan Full Prescribing Information-Novartis. WO2015095257 discloses treating diabetes or diabetic retinopathy with dopamine, and in embodiments the dopamine is administered in combination with a COMT inhibitor, such as entacapone, tolcapone, or nitecapone.

Here we disclose the use of entacapone and related formulations to treat macular degeneration or age-related macular degeneration.

SUMMARY OF THE INVENTION

The invention provides entacapone-related compounds, compositions and methods to treat or inhibit macular degeneration, particularly age-related macular degeneration.

In an aspect the invention provides a use or method of use of entacapone, an entacapone derivative or a stereoisomer, hydride, or pharmaceutically-acceptable salt thereof, in a person in need thereof, to treat or inhibit macular degeneration or age-related macular degeneration, preferably wherein the person does not have Parkinson's disease, obesity, diabetes or diabetic retinopathy.

The invention may be practiced with a wide variety of entacapone derivatives, and activity is readily confirmed empirically; exemplary suitable derivatives are disclosed in U.S. Pat. No. 5,112,861, WO2007144169, EP1978014A1 and WO/2016/206573. In particular embodiments the derivatives FTO inhibitors.

In a particular embodiment the entacapone derivative comprises a structure of formula I of WO/2016/206573, a stereoisomer thereof, a hydride thereof, or a pharmaceutically-acceptable salt thereof:

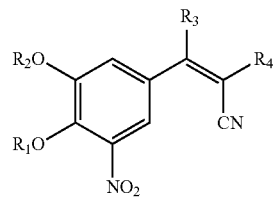

wherein:

R1 and R2 are independently H or Me;

R3 is H, OH or NHR, wherein R is H or an optionally substituted, optionally hetero-, optionally cyclic C1-C18 hydrocarbyl; and R4 is optionally substituted, optionally hetero-, optionally cyclic C1-C18 hydrocarbyl.

In a particular embodiment the entacapone derivative comprises a structure of formula I of U.S. Pat. No. 5,112,861, a stereoisomer thereof, a hydride thereof, or a pharmaceutically-acceptable salt thereof:

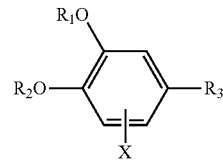

wherein R1 and R2 independently represent hydrogen, alkylcarbamoyl of 2 to 5 carbon atoms or alkylcarbonyl of 2 to 5 carbon atoms, X represents nitro or cyano and R3 represents

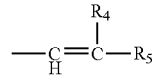

wherein R4 represents cyano or alkylcarbonyl of 2 to 5 carbon atoms and R5 represents cyano; alkylcarbonyl of 2 to 5 carbon atoms; or carbamoyl which is unsubstituted or substituted with alkyl of 1 to 8 carbon atoms, or hydroxyalkyl of 1 to 8 carbon atoms.

In a particular embodiment the entacapone derivative comprises a structure of formula I of WO2007144169, a stereoisomer thereof, a hydride thereof, or a pharmaceutically-acceptable salt thereof:

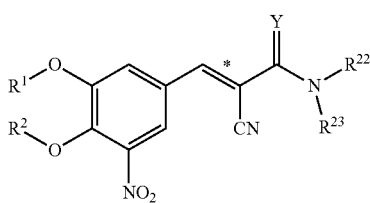

(I)

wherein
Y is sulfur or oxygen,
$R^1$ is a group of the following formula II

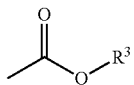

(II)

or when Y is S, $R^1$ can be in addition H,
$R^2$ is H or a group of formula II which may be the same as or different from $R^1$,
each $R^3$ is independently $(C_1-C_{20})$-alkyl, $(CR^4R5)x-R^6$, $(C_rC_{20})$-alkylene-$(C_1-C_{20})$-alkoxy, $(C_2-C_{20})$-alkenyl, $(C_2-C_{20})$-alkynyl, $(C_0-C_{20})$-alkylene-$(C_3-C_{18})$-cycloalkyl, $(C_0-C_{20})$-alkylene-(3-18-membered)-heterocycloalky l, $(C_1-C_{20})$-alkylene-$(C_3-C_{18})$-cycloalkenyl, $(C_0-C_{20})$-alkylene-(3-18-membered)-heterocycloalkenyl, $(C_0-C_{20})$-alkylene-$(C_6-C_{18})$-aryl, $(C_0-C_{20})$-alkylene-(5-18-membered)-heteroaryl, $(C_2-C_{20})$-alkenylene-$(C_3-C_{18})$-cycloalkyl, $(C_2-C_{20})$-alkenylene-(3-18-membered)-heterocycloalkyl, $(C_2-C_{20})$-alkenylene-$(C_3-C_{18})$-cycloalkenyl, $(C_2-C_{20})$-alkenylene-(3-18-membered)-heterocycloalkenyl, $(C_2-C_{20})$-alkenylene-$(C_6-C_{18})$-aryl, or $(C_2-C_{20})$-alkenylene-(5-18-membered)-heteroaryl,
wherein the total number of carbon atoms of $R^3$ is at most 30,
each $R^4$ and $R^5$ are independently of one another selected from the group consisting of H, $(C_1-C_{20})$-alkyl, $(C_1-C_{20})$-alkylene-hydroxy, $(C_0-C_{20})$-alkylene-$(C,-C_{20})$-alkoxy, OH, $(C_0-C_{20})$-alkylene-$N(R^7)CO$—$(C,-C_{20})$-alkyl, $(C_0-C_{20})$-alkylene-$CON(R^8)(R^9)$, $(C_0-C_{20})$-alkylene-COO—$(C_1-C_{20})$-alkyl, $(C_0-C_{20})$-alkylene-$N(R^{10})(R^\pi)$, $SO_3R^{17}$, $(C_0-C_{20})$-alkylene-$(C_6-C_{18})$-aryl, and $(C_0-C_{20})$-alkylene-(5-18-membered)-heteroaryl,
or
$R^4$ and $R^5$ of the same group $(CR^4R^5)$ or $R^4$ and $R^5$ of different groups $(CR^4R^5)$ may form together a carbocyclic or heterocyclic ring having from 3 to 6 atoms,
additionally, one or more non adjacent groups $(CR^4R^5)$ may be replaced by O, CO, OCO, COO, $CON(R^{19})$, $N(R^{20})CO$, or $NR^{21}$,
$R^6$ is independently H, $(C_rC_{20})$-alkyl, $(C_2-C_{20})$-alkenyl, $(C_2-C_{20})$-alkynyl, OH, O—$(C_rC_8)$-alkyl, O—$(C_0-C_8)$-alkylene-$(C_6-C_{14})$-aryl, CO—O—$(C,-C_8)$-alkyl, CO—$N(R^{12})(R^{13})$, $N(R^{14})CO$—$(C_1-C_8)$-alkyl, $N(R^{15}XR^{16})$, $SO_3R^{18}$, $(C_0-C_{20})$-alkylene-(5-18-membered)-heteroaryl, or $(C_0-C_{20})$-alkylene-$(C_6-C_{18})$-aryl,
$R^7$, $R^{14}$, $R^{17}$, $R^{18}$, $R^{19}$, $R^{20}$, $R^{21}$ are independently of one another H, or $(C_1-C_{20})$-alkyl,
$R^8$, $R^9$, $R^{10}$, $R^{11}$, $R^{12}$, $R^{13}$, $R^{15}$, $R^{16}$ are independently of one another H, or $(C_1-C_{20})$-alkyl,
$R^{22}$ and $R^{23}$ are independently selected from the group consisting of H and $(C_1-C_{15})$-alkyl, and
x is 1 to 14, wherein the alkyl, alkenyl, alkynyl, cycloalkyl, heterocycloalkyl, cycloalkenyl, heterocycloalkenyl, alkoxy, aryl, heteroaryl, alkenylene and alkylene groups may be unsubstituted or further substituted.

In embodiments the use further comprises the step of detecting a resultant inhibition of macular degeneration.

In other aspects the invention provides a pharmaceutical composition or formulation comprising:

a) an ophthalmic composition comprising entacapone, an entacapone derivative or a stereoisomer, hydride, or pharmaceutically-acceptable salt thereof, wherein the composition does not include dopamine or a dopamine derivative, such as levodopa (L-DOPA) or carbidopa;

b) a topical ophthalmic composition comprising entacapone, an entacapone derivative or a stereoisomer, hydride, or pharmaceutically-acceptable salt thereof; or c) a composition comprising entacapone, an entacapone derivative or a stereoisomer, hydride, or pharmaceutically-acceptable salt thereof, copackaged or coformulated with a second, different medicament for treating or inhibiting macular degeneration or age-related macular degeneration.

In embodiments:

the composition or formulation does not include another anti-Parkinsons medicament, neuroactive agent, anti-obesity, anti-diabetes, and/or another active pharmaceutical ingredient (API), such as wherein anti-Parkinson's medicaments include L-DOPA, deprenyl, tyrosine hydroxylase, apomorphine, anticholinergic drugs such as benzhexol and orphenadrine, and mGluR4 potentiators such as N-phenyl-7-(hydroxylimino)cyclopropa[b]chromen-1a-carboxamide (PHCCC);

the composition or formulation is in topical form of eye drops, ointments, gels, or emulsions;

the composition or formulation is in form of an intravitreal injection formulation or an intraocular implant formulation;

the composition or formulation wherein the entacapone, entacapone derivative or pharmaceutically-acceptable salt thereof, is in unit dosage form; and/or the composition or formulation wherein the second medicament is an antiangiogenic drug (e.g. VEGF inhibitor) selected from revacizumab, ranibizumab, pegaptanib, and aflibercept.

In embodiments, the entacapone, an entacapone derivative or a stereoisomer, hydride, or pharmaceutically-acceptable salt thereof is administered to the eye in topical form of eye drops, ointments, gels, or emulsions, or into the vitreous or sclera of the eye, e.g., administered by an intravitreal injection or an implant, e.g., surgical administration of drug-loaded solid implants within the scleral tissue (i.e. intrascleral delivery); see, e.g. Falavarjani et al., Eye (2013) 27, 787-794; Adverse events and complications associated with intravitreal injection of anti-VEGF agents: a review of literature; Marra, et al. AAPS PharmSciTech. 2011 March; 12(1): 362-371. Solution Formulation Development of a VEGF Inhibitor for Intravitreal Injection, etc.

The invention encompasses all combination of the particular embodiments recited herein, as if each had been separately, laboriously recited.

DESCRIPTION OF PARTICULAR EMBODIMENTS OF THE INVENTION

Figure 1:
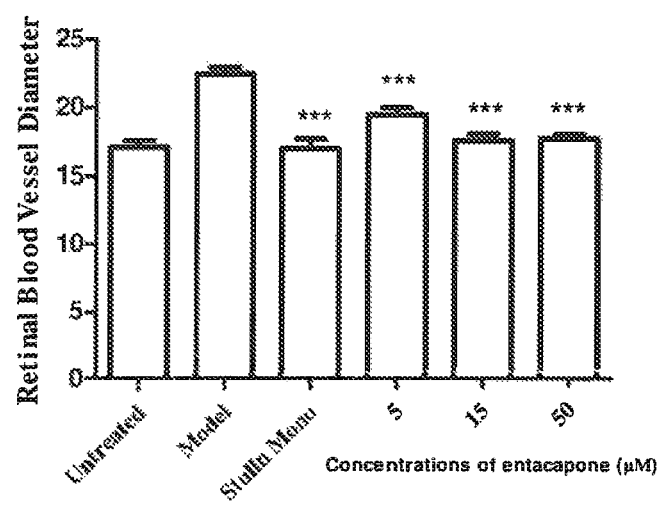
FIG. 1. The eye blood vessel diameter. Values are presented as mean±SE (n=10). ***p<0.001, compared with the model group.

The following descriptions of particular embodiments and examples are provided by way of illustration and not by way of limitation. Those skilled in the art will readily recognize a variety of noncritical parameters that could be changed or modified to yield essentially similar results.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

A hydrocarbyl group is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which comprises 1-15 carbon atoms and optionally includes one or more heteroatoms in its carbon skeleton.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2$—$CH_2$—$CH_2$—$CH_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$.

Similarly, the term "heteroalkylene," by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-,6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO2R', —NR'—C(O)NR"R'", —NR'—SO$_2$NR"R'", —NH—C(NH2)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alko-xy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O) R', —OC(O)NR'R", —NR"C(O)R', —S(O)R', —SO$_2$R', —SO$_2$NR'R", —NR"SO$_2$R, —N$_3$, —CH(Ph)$_2$, perfluoro (C1-C4)alkoxy and perfluoro(C1l-C4)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4) alkoxy and perfluoro(C1-C4)alkyl.

The substituent —CO$_2$H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)q-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C1-C6)alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, optionally heteroatom C1-C6 alkyl, substituted or unsubstituted, optionally heteroatom C2-C6 alkenyl, substituted or unsubstituted, optionally heteroatom C2-C6 alkynyl, or substituted or unsubstituted, optionally heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The term "pharmaceutically acceptable salts" is meant to include salts of the active compounds which are prepared with relatively nontoxic acids or bases, depending on the particular substituents found on the compounds described herein, and suitable for pharmaceutical use. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Some of the subject compounds possess asymmetric carbon atoms (optical centers) or double bonds; the racemates, diastereomers, geometric isomers and specifically designated or depicted chirality is preferred and in many cases critical for optimal activity; however all such isomers are all intended to be encompassed within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the compounds may be advantageously used in conjunction with other therapeutic agents as described herein or otherwise known in the art, particularly other anti-necrosis agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 5, 25 or 100 to about 5, 25, 100, 500, 1000 or 2000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10, 100, 1000, 10000, 20000 ug/kg to about 10, 100, 1000, 10000, 20000 or 80000 ug/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

In particular embodiments the subject entacapone derivative comprises a structure of formula I of WO/2016/206573, a stereoisomer thereof, a hydride thereof, or a pharmaceutically-acceptable salt thereof:

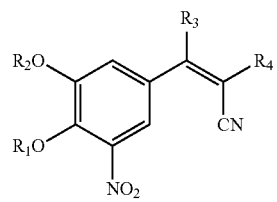

wherein:

(a)

R1 and R2 are independently H or Me;

R3 is OH or NHR, wherein R is H or an optionally substituted, optionally hetero-, optionally cyclic C1-C18 hydrocarbyl; and R4 is optionally substituted, optionally hetero-, optionally cyclic C1-C18 hydrocarbyl;

(b)

R1 and R2 are independently H or Me;

R3 is H, OH or NHR, wherein R is H or C1-C4 alkyl;

R4 is CONHR5; and

R5 is optionally substituted, optionally hetero-, optionally cyclic C1-C18 hydrocarbyl;

(c)

R1 and R2 are independently H or Me;

R3 is H, OH or NHR, wherein R is H or C1-C4 alkyl;

R4 is COR5; and

R5 is optionally substituted, heterocyclic C3-C18 hydrocarbyl comprising an n-membered ring wherein n=3-18 including 1 to n−1 heteroatoms independently selected from N, O, S and P; or (d)
R1 and R2 are independently H or Me;
R3 is H, OH or NHR, wherein R is H or C1-C4 alkyl; and
R4 is optionally substituted, heterocyclic C3-C18 hydrocarbyl comprising an n-membered ring wherein n=3-18 including 1 to n−1 heteroatoms independently selected from N, O, S and P; particularly wherein excluded from the inhibitor are compounds: CAS IDS: 1364322-41-7, 1150310-12-5, 1150310-15-8, and 143542-72-7.

In embodiments of the inhibitor or composition the heterocyclic C3-C18 hydrocarbyl comprises:
a 3 membered ring that is an optionally substituted: aziridine, oxirane, oxaziridine;
a 4 membered ring that is an optionally substituted: azetidine, oxetane, oxazetidine;
a 5 membered ring that is an optionally substituted: pyrrole, 1,2-diazole (pyrazole), 1,3 diazole (imidazole), thiazole, isothiazole, oxazole, isoxazole, furan, dioxole, thiophene;
a 6 membered ring that is an optionally substituted: pyridine, diazine, triazine, oxazine, thiazine, dioxine, oxathiine, dithiine;
a 9 membered ring that is an optionally substituted: indole, benzothiazole, benzooxazole, benzofuran, benzodioxole, benzothiophene, benzodithiole; or
a 10 membered ring that is an optionally substituted: quinoline, quinoxaline, quinazoline, chromene, benzodioxine, thiochromene, benzodithiine.

In embodiments of the inhibitor or composition the optionally substituted, optionally hetero-, optionally cyclic C1-C18 hydrocarbyl in each instance is an optionally substituted C1-C9 alkyl, C2-C9 alkenyl, C2-C9 alkynyl, or C5-C14 aryl hydrocarbon, comprising 1-5 heteroatoms that are N, S, O or P, including 1-5 nitrogen atoms, or a heteroatom substituted with the hydrocarbon.

In embodiments of the inhibitor or composition:
one or both R1 and R2 is H;
R3 is OH; and/or
R is H or C1-C4 alkyl, esp. Me.

The invention encompasses all combination of the particular embodiments recited herein, as if each had been separately, laboriously recited. For example, subsection (a) encompasses combinations wherein: R1 and R2 are H; R3 is NH$_2$; and R4 is a 6 membered ring that is pyridine, and subsection (d) encompasses combinations wherein R1 and R2 are Me; R3 is OH; and R4 is 1,3 diazole.

In embodiments the inhibitor is of the following Tables.

TABLE 1

Subsection (a) inhibitors

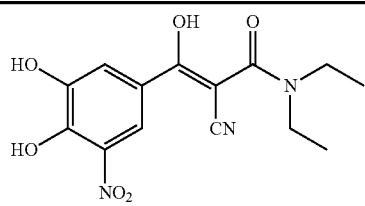

347

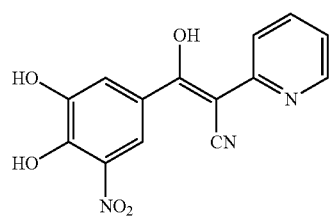

351

TABLE 1-continued

Subsection (a) inhibitors

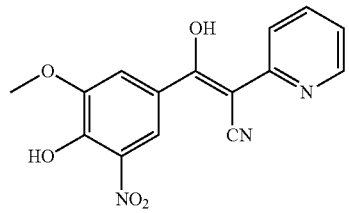 [SMILES: COc1cc(/C(O)=C(\C#N)c2ccccn2)cc([N+](=O)[O-])c1O]

352

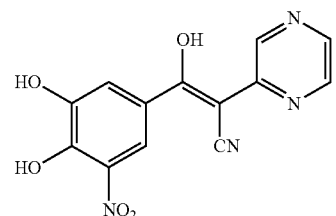

523

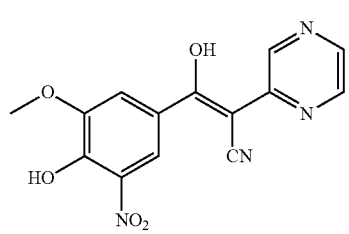 [SMILES: COc1cc(/C(O)=C(\C#N)c2cnccn2)cc([N+](=O)[O-])c1O]

524

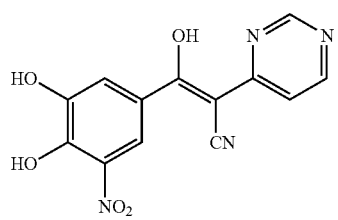 [SMILES: N#C/C(=C(/O)c1cc(O)c(O)c([N+](=O)[O-])c1)c1ccncn1]

525

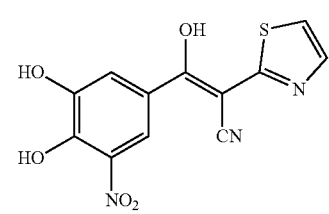 [SMILES: N#C/C(=C(/O)c1cc(O)c(O)c([N+](=O)[O-])c1)c1nccs1]

503

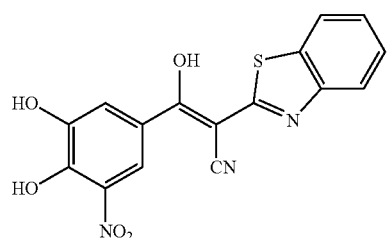

359

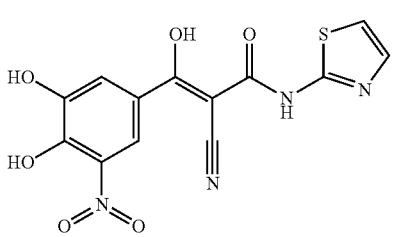 [SMILES: N#C/C(C(=O)Nc1nccs1)=C(/O)c1cc(O)c(O)c([N+](=O)[O-])c1]

374

TABLE 1-continued

Subsection (a) inhibitors

TABLE 2
| Subsection (a) inhibitors. | |
|---|---|
| 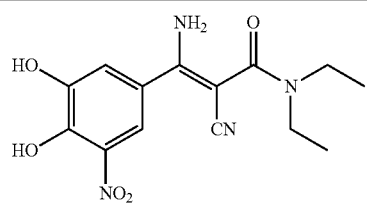 [SMILES: CCN(CC)C(=O)/C(C#N)=C(\N)c1cc(O)c(O)c([N+](=O)[O-])c1] | 347N |
| 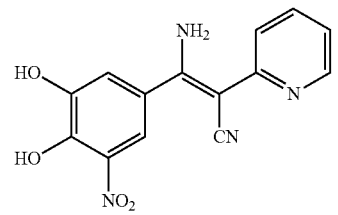 [SMILES: N#C/C(=C(/N)c1cc(O)c(O)c([N+](=O)[O-])c1)c1ccccn1] | 351N |
| 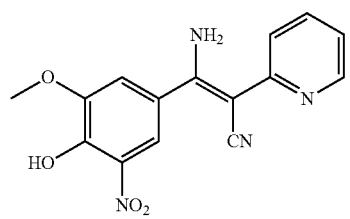 [SMILES: COc1cc(/C(N)=C(\C#N)c2ccccn2)cc([N+](=O)[O-])c1O] | 352N |
| 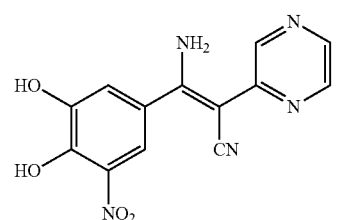 | 523N |
| 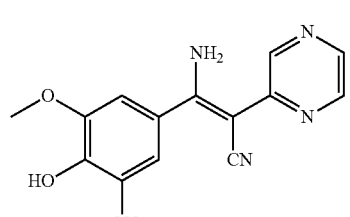 | 524N |
| 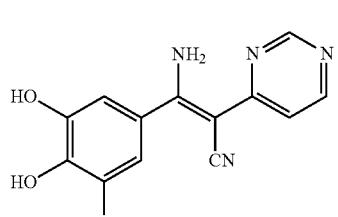 | 525N |
| 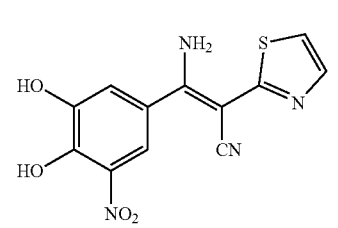 | 503N |
TABLE 2-continued
| Subsection (a) inhibitors. | |
|---|---|
| 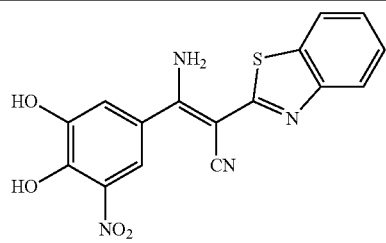 | 359N |
| 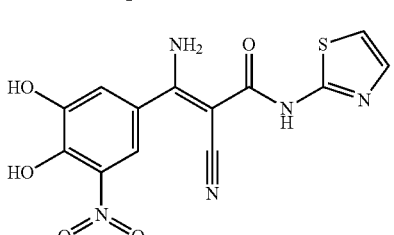 | 374N |
| 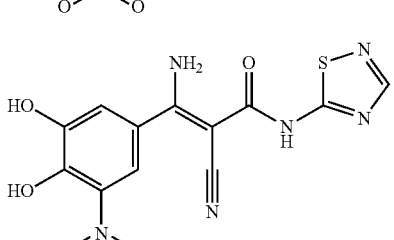 | 668N |
| 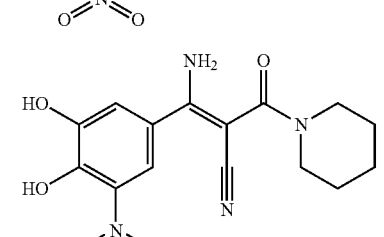 | 661N |
| 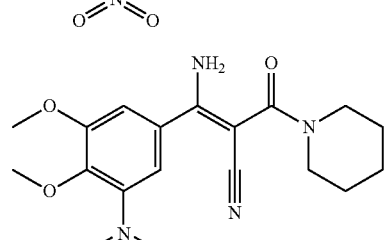 | 658N |
| 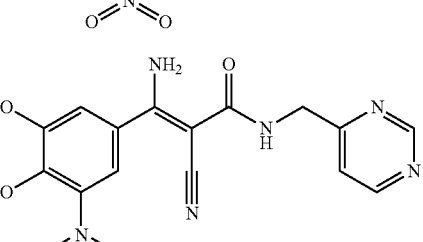 | 673N |
| 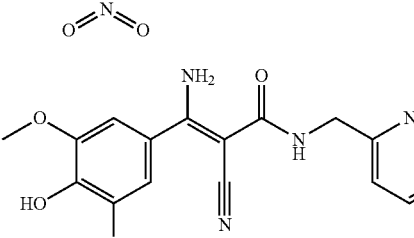 | 674N |

TABLE 2-continued
Subsection (a) inhibitors.
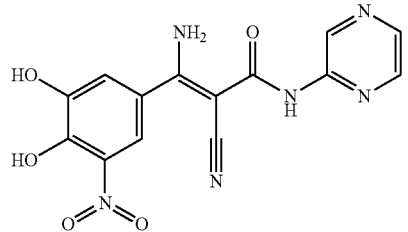 [SMILES: N#C/C(C(=O)Nc1cnccn1)=C(/N)c1cc(O)c(O)c([N+](=O)[O-])c1]
722N
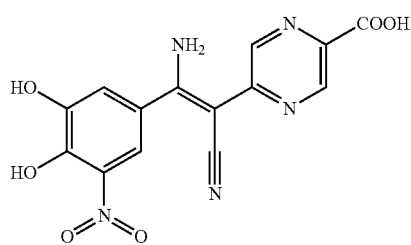
697N
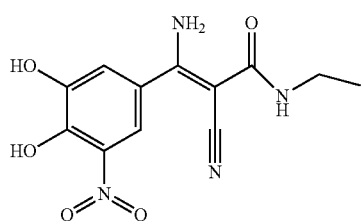 [SMILES: CCNC(=O)/C(C#N)=C(\N)c1cc(O)c(O)c([N+](=O)[O-])c1]
691N
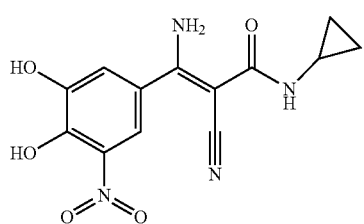
692N
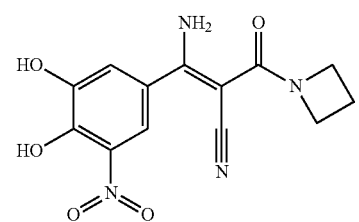
701N
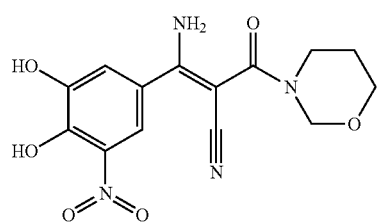 [SMILES: N#C/C(C(=O)N1CCCOC1)=C(/N)c1cc(O)c(O)c([N+](=O)[O-])c1]
715N
TABLE 2-continued
Subsection (a) inhibitors.
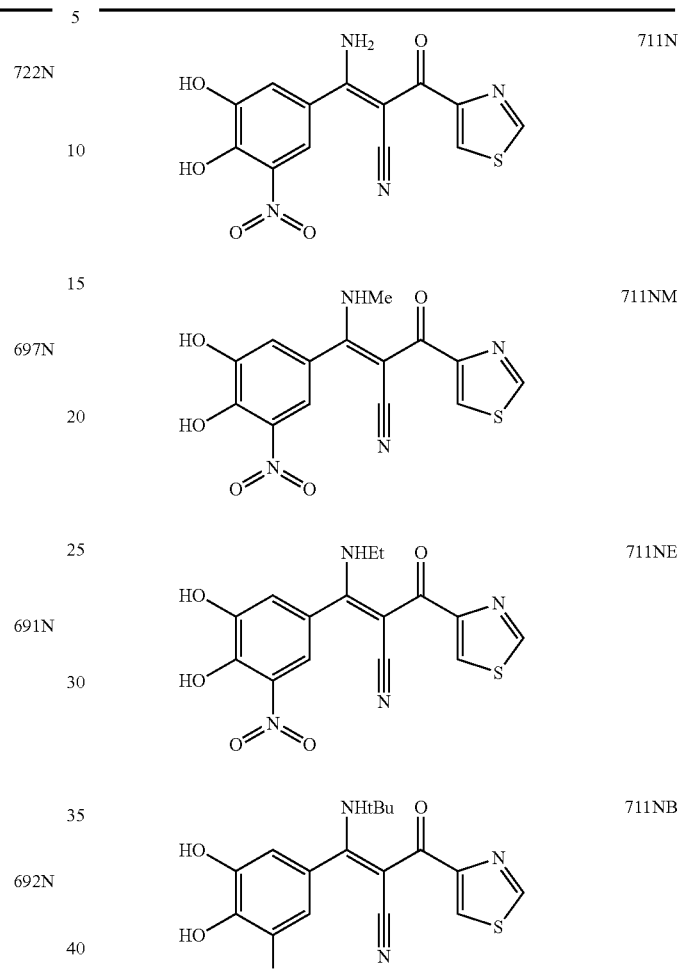
711N
711NM
711NE
711NB
TABLE 3
Subsection (b) inhibitors.
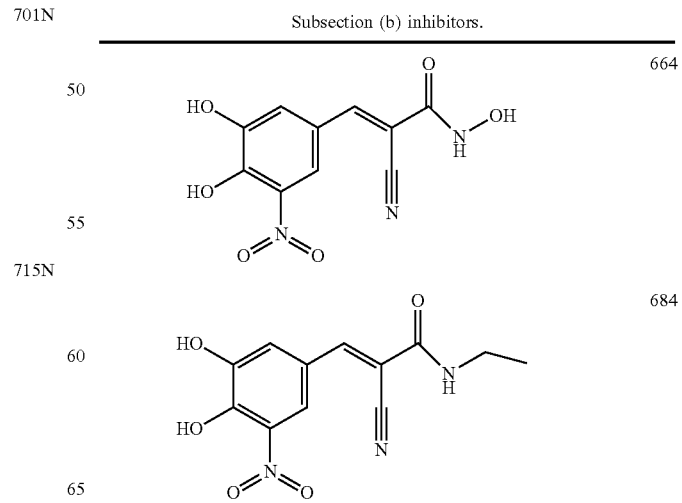
664
684

TABLE 3-continued
Subsection (b) inhibitors.
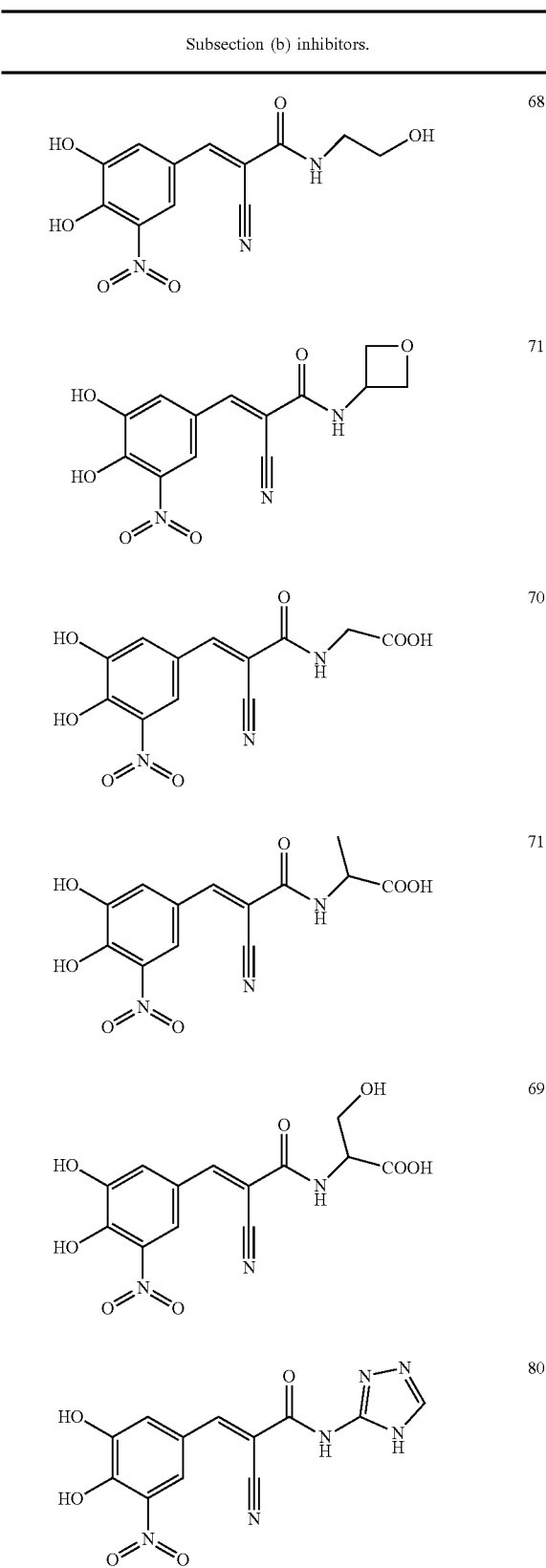
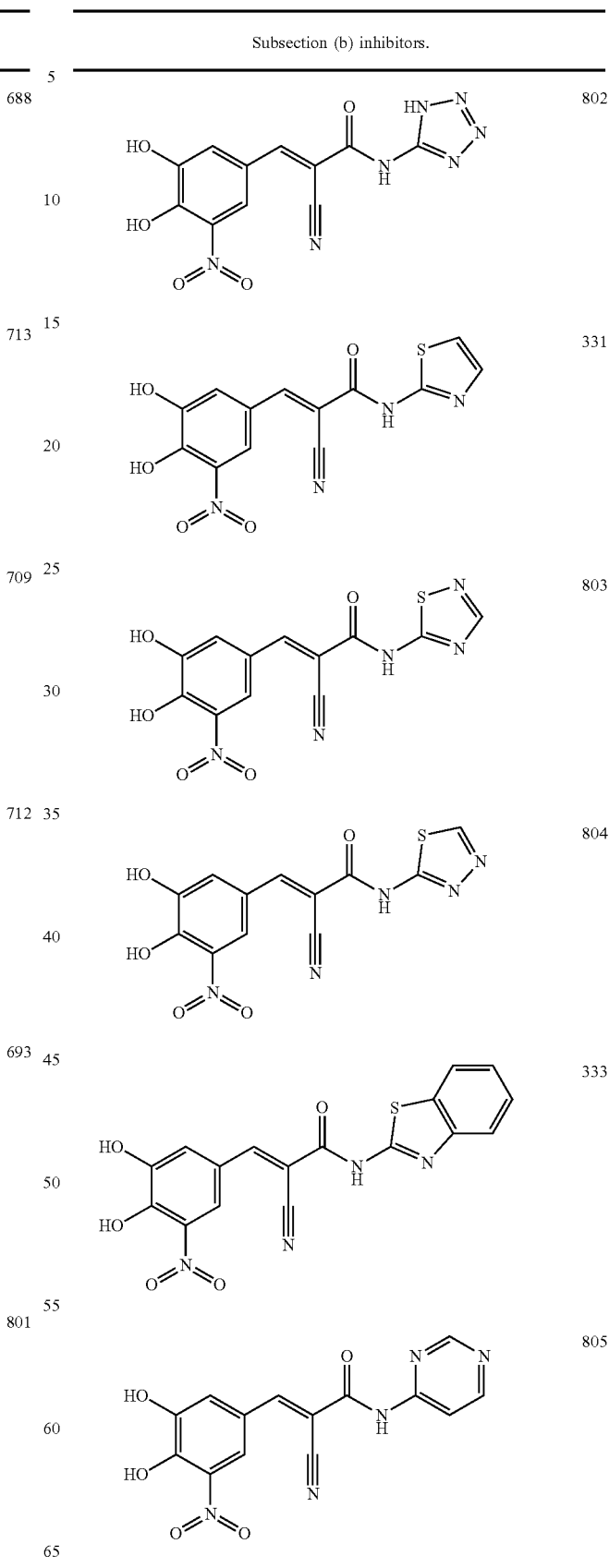

TABLE 3-continued
Subsection (b) inhibitors.
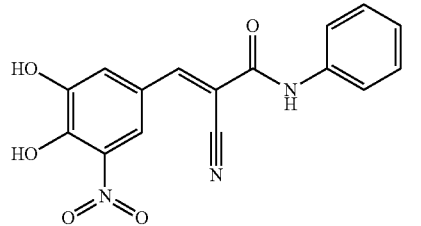 [SMILES: N#C/C(=C\c1cc(O)c(O)c([N+](=O)[O-])c1)C(=O)Nc1ccccc1] 318
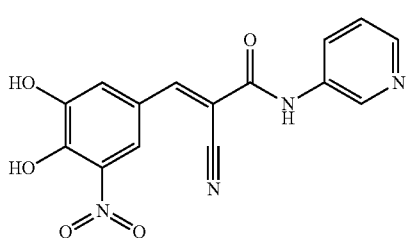 [SMILES: N#C/C(=C\c1cc(O)c(O)c([N+](=O)[O-])c1)C(=O)Nc1cccnc1] 806
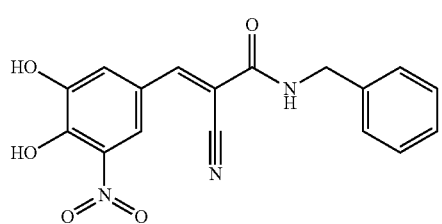 [SMILES: N#C/C(=C\c1cc(O)c(O)c([N+](=O)[O-])c1)C(=O)NCc1ccccc1] 366
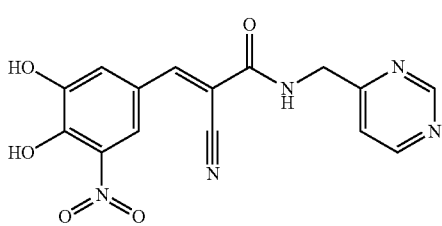 [SMILES: N#C/C(=C\c1cc(O)c(O)c([N+](=O)[O-])c1)C(=O)NCc1ccncn1] 807
CAS ID: 1150310-12-5 365
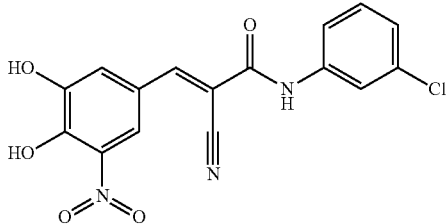
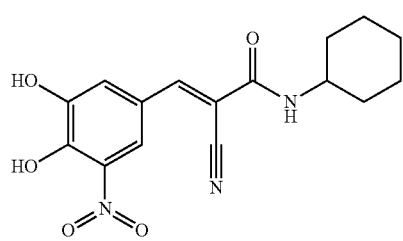 [SMILES: N#C/C(=C\c1cc(O)c(O)c([N+](=O)[O-])c1)C(=O)NC1CCCCC1] 380
TABLE 3-continued
Subsection (b) inhibitors.
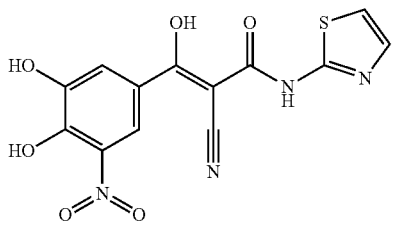 [SMILES: N#C/C(C(=O)Nc1nccs1)=C(/O)c1cc(O)c(O)c([N+](=O)[O-])c1] 374
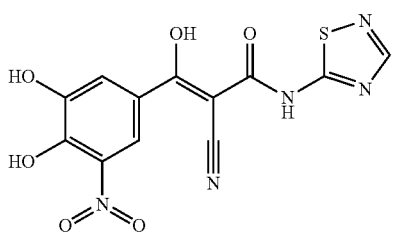 [SMILES: N#C/C(C(=O)Nc1ncns1)=C(/O)c1cc(O)c(O)c([N+](=O)[O-])c1] 668
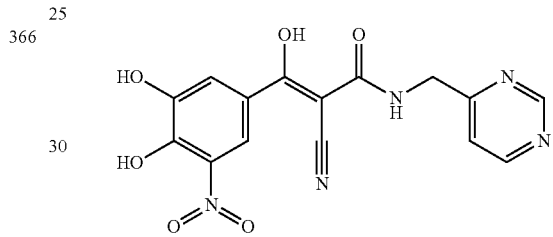 673
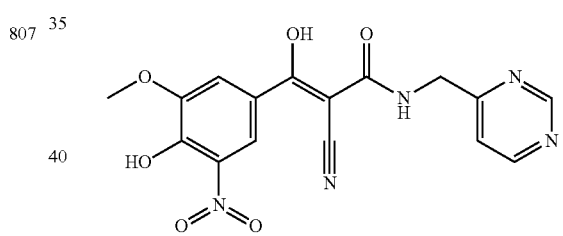 674
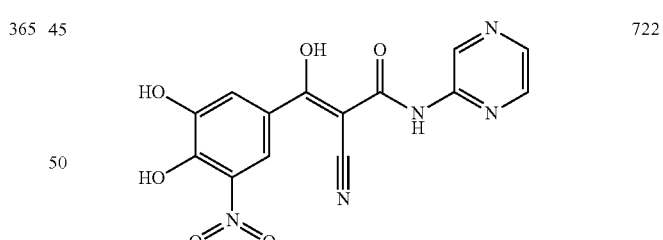 722
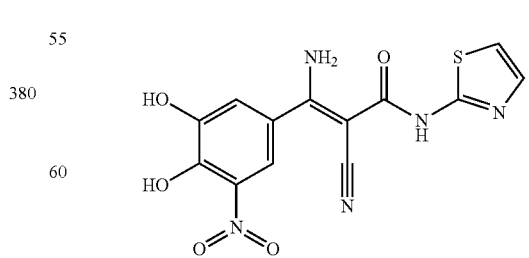 374N TABLE 4
Subsection (c) inhibitors.
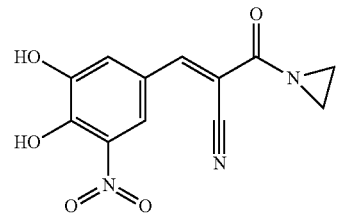 [SMILES: N#C/C(=C\c1cc(O)c(O)c([N+](=O)[O-])c1)C(=O)N1CC1] 808
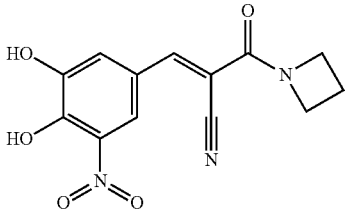 [SMILES: N#C/C(=C\c1cc(O)c(O)c([N+](=O)[O-])c1)C(=O)N1CCC1] 687
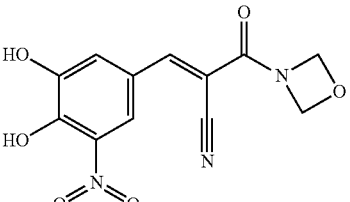 809
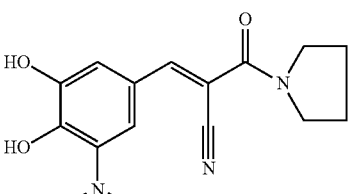 317
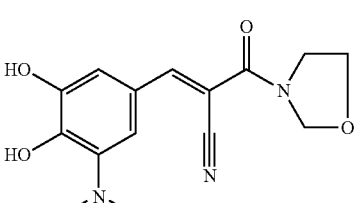 810
CAS ID: 1150310-15-8
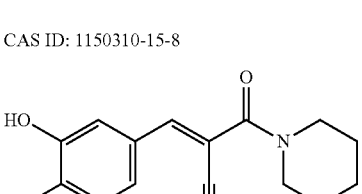 371
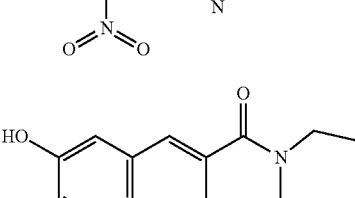 378

TABLE 4-continued
Subsection (c) inhibitors.
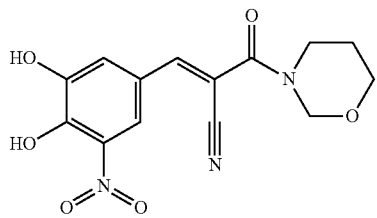 [SMILES: N#C/C(=C\c1cc(O)c(O)c([N+](=O)[O-])c1)C(=O)N1CCCOC1] 660
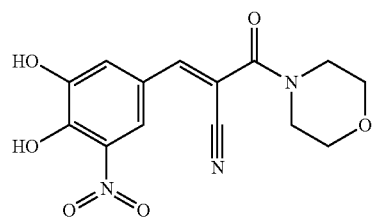 [SMILES: N#C/C(=C\c1cc(O)c(O)c([N+](=O)[O-])c1)C(=O)N1CCOCC1] 382
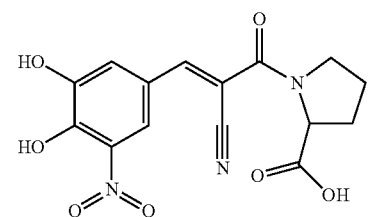 [SMILES: N#C/C(=C\c1cc(O)c(O)c([N+](=O)[O-])c1)C(=O)N1CCCC1C(=O)O] 702
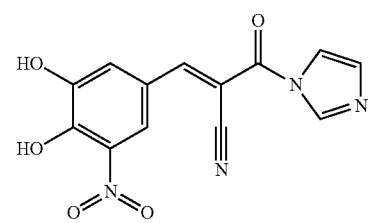 [SMILES: N#C/C(=C\c1cc(O)c(O)c([N+](=O)[O-])c1)C(=O)n1ccnc1] 811
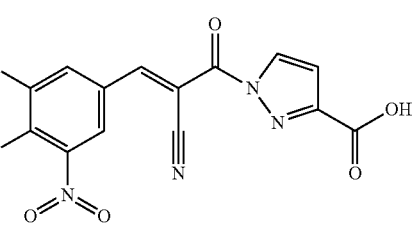 812
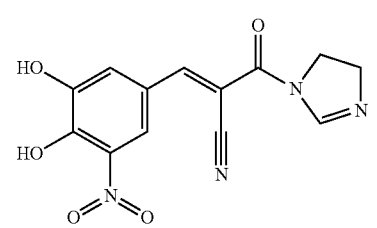 [SMILES: N#C/C(=C\c1cc(O)c(O)c([N+](=O)[O-])c1)C(=O)N1C=NCC1] 813
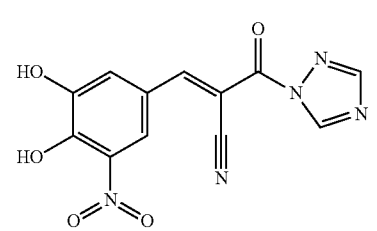 [SMILES: N#C/C(=C\c1cc(O)c(O)c([N+](=O)[O-])c1)C(=O)n1cncn1] 814
TABLE 4-continued
Subsection (c) inhibitors.
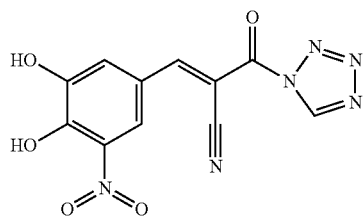 [SMILES: N#C/C(=C\c1cc(O)c(O)c([N+](=O)[O-])c1)C(=O)n1cnnn1] 815
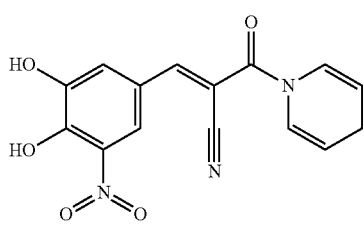 [SMILES: N#C/C(=C\c1cc(O)c(O)c([N+](=O)[O-])c1)C(=O)N1C=CCC=C1] 816
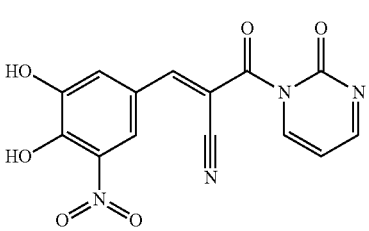 [SMILES: N#C/C(=C\c1cc(O)c(O)c([N+](=O)[O-])c1)C(=O)n1cccnc1=O] 817
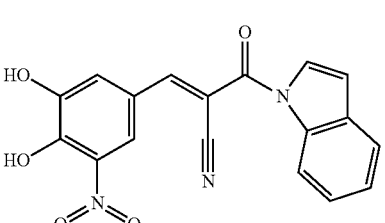 818
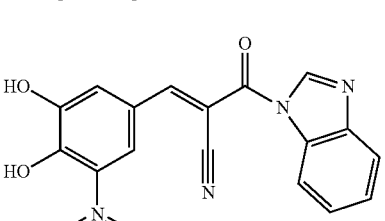 819
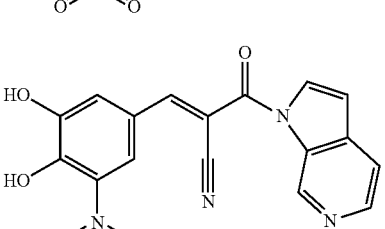 820
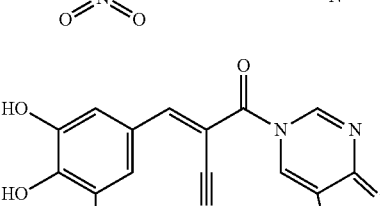 821

TABLE 4-continued

Subsection (c) inhibitors.

TABLE 4-continued

Subsection (c) inhibitors.

| Structure | No. |
|---|---|
| (3,4-dihydroxy-5-nitrophenyl)(amino)-cyanovinyl thiazol-4-yl ketone | 711N |
| (3,4-dihydroxy-5-nitrophenyl)(amino)-cyanovinyl piperidin-1-yl ketone | 661N |
| (3,4-dimethoxy-5-nitrophenyl)(amino)-cyanovinyl piperidin-1-yl ketone | 658N |
| (3,4-dihydroxy-5-nitrophenyl)(amino)-cyanovinyl azetidin-1-yl ketone | 701N |
| (3,4-dihydroxy-5-nitrophenyl)(amino)-cyanovinyl morpholin-1-yl ketone | 715N |

TABLE 5

Subsection (d) inhibitors.

| Structure | No. |
|---|---|
| 3-(3,4-dihydroxy-5-nitrophenyl)-2-(thiazol-2-yl)acrylonitrile | 390 |
| 3-(3,4-dihydroxy-5-nitrophenyl)-2-(1,2,3,4-thiadiazol-5-yl)acrylonitrile | 656 |
| 2-(3,4-dihydroxy-5-nitrostyryl)thiazole-4-carboxylic acid | 666 |
| 3-(3,4-dihydroxy-5-nitrophenyl)-2-(benzothiazol-2-yl)acrylonitrile | 829 |
| 3-(3,4-dihydroxy-5-nitrophenyl)-2-(pyridin-2-yl)acrylonitrile | 315 |
| 3-(3-hydroxy-4-methoxy-5-nitrophenyl)-2-(pyridin-2-yl)acrylonitrile | 400 |
| 3-(3,4-dihydroxy-5-nitrophenyl)-2-(pyridin-3-yl)acrylonitrile | 319 |
| 3-(3,4-dihydroxy-5-nitrophenyl)-2-(pyridin-4-yl)acrylonitrile | 389 |

TABLE 5-continued
Subsection (d) inhibitors.
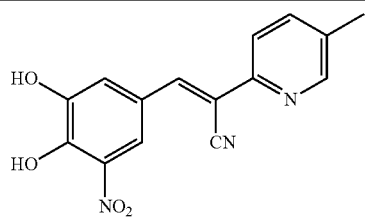 502
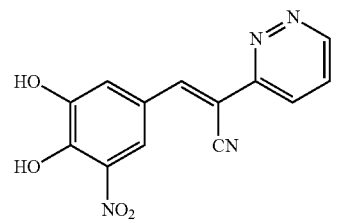 [SMILES: N#C/C(=C\c1cc(O)c(O)c([N+](=O)[O-])c1)c1cccnn1] 505
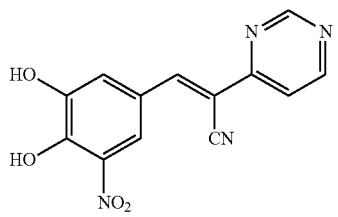 [SMILES: N#C/C(=C\c1cc(O)c(O)c([N+](=O)[O-])c1)c1ccncn1] 395
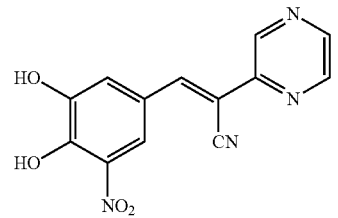 [SMILES: N#C/C(=C\c1cc(O)c(O)c([N+](=O)[O-])c1)c1cnccn1] 396
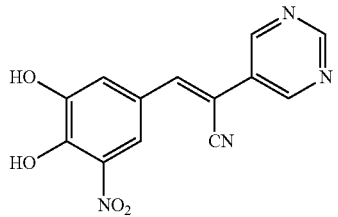 [SMILES: N#C/C(=C\c1cc(O)c(O)c([N+](=O)[O-])c1)c1cncnc1] 522
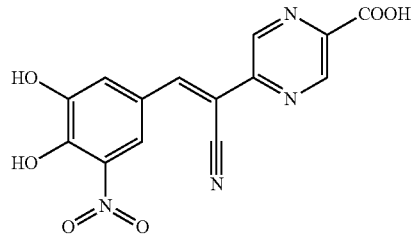 [SMILES: N#C/C(=C\c1cc(O)c(O)c([N+](=O)[O-])c1)c1cnc(C(=O)O)cn1] 655
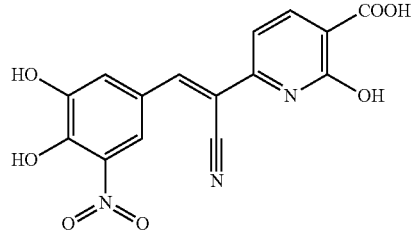 [SMILES: N#C/C(=C\c1cc(O)c(O)c([N+](=O)[O-])c1)c1ccc(C(=O)O)c(O)n1] 830
TABLE 5-continued
Subsection (d) inhibitors.
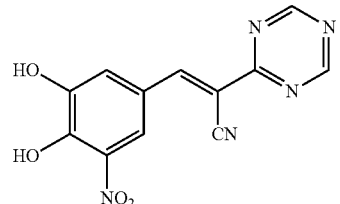 831
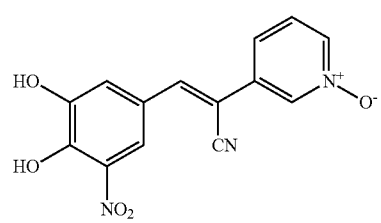 [SMILES: N#C/C(=C\c1cc(O)c(O)c([N+](=O)[O-])c1)c1ccc[n+]([O-])c1] 518
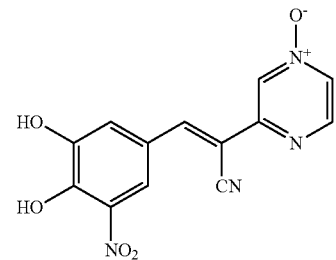 [SMILES: N#C/C(=C\c1cc(O)c(O)c([N+](=O)[O-])c1)c1c[n+]([O-])ccn1] 520
CAS ID: 143542-72-7
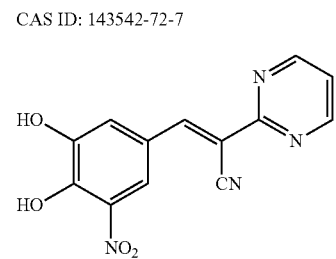 361
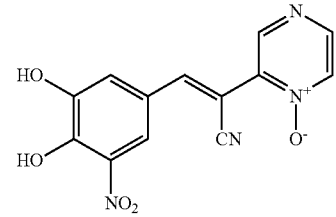 [SMILES: N#C/C(=C\c1cc(O)c(O)c([N+](=O)[O-])c1)c1cncc[n+]1[O-]] 517
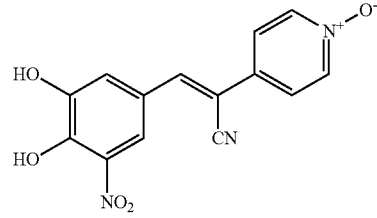 [SMILES: N#C/C(=C\c1cc(O)c(O)c([N+](=O)[O-])c1)c1cc[n+]([O-])cc1] 519

TABLE 5-continued
Subsection (d) inhibitors.
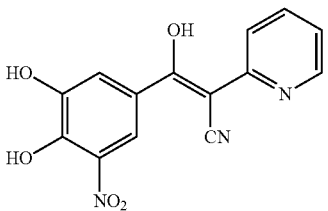 [SMILES: N#C/C(=C(/O)c1cc(O)c(O)c([N+](=O)[O-])c1)c1ccccn1] 351
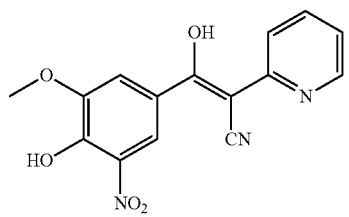 [SMILES: COc1cc(/C(O)=C(\C#N)c2ccccn2)cc([N+](=O)[O-])c1O] 352
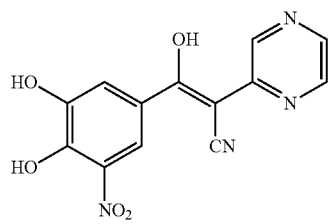 523
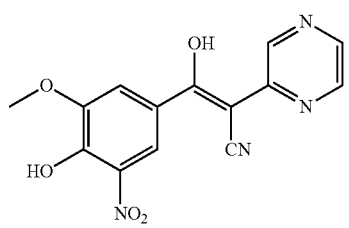 [SMILES: COc1cc(/C(O)=C(\C#N)c2cnccn2)cc([N+](=O)[O-])c1O] 524
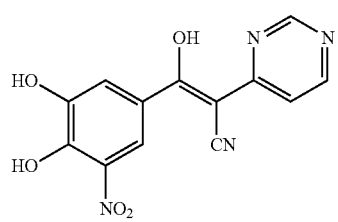 525
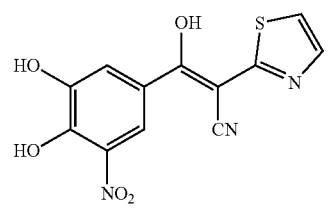 [SMILES: N#C/C(=C(/O)c1cc(O)c(O)c([N+](=O)[O-])c1)c1nccs1] 503
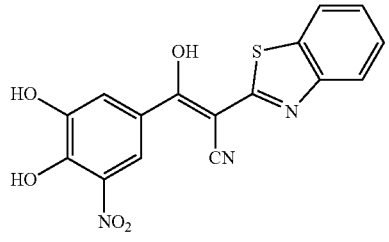 [SMILES: N#C/C(=C(/O)c1cc(O)c(O)c([N+](=O)[O-])c1)c1nc2ccccc2s1] 359
TABLE 5-continued
Subsection (d) inhibitors.
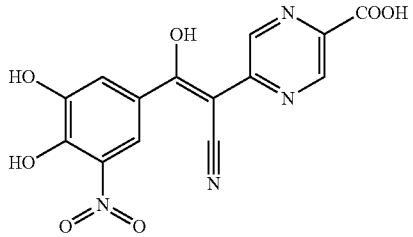 [SMILES: N#C/C(=C(/O)c1cc(O)c(O)c([N+](=O)[O-])c1)c1cnc(C(=O)O)cn1] 697
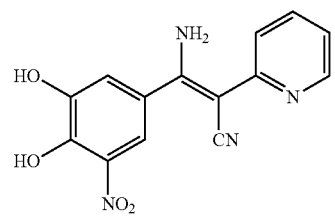 351N
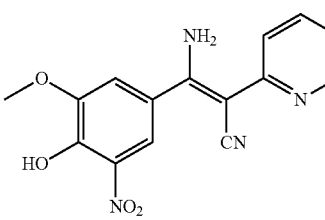 352N
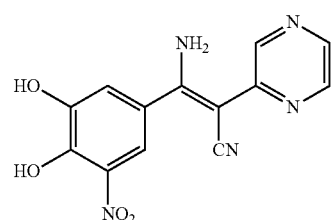 523N
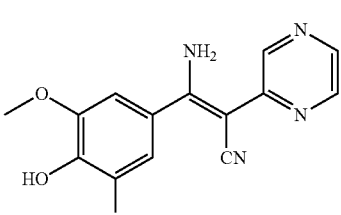 524N
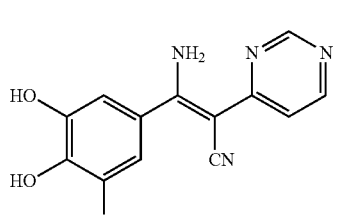 525N
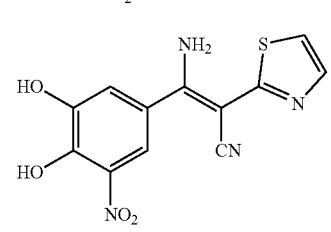 503N TABLE 5-continued Subsection (d) inhibitors.

359N

[Structure: benzothiazole derivative with NH2, CN, NO2, and two HO groups on phenyl]

697N

[Structure: pyrazine-COOH derivative with NH2, CN, NO2, and two HO groups on phenyl]

Compound Preparation.

EP1978014 discloses processes for preparing entacapone; synthesis of representative derivatives are fully disclosed in WO/2016/206573, and not repeated here.

Therapeutic Activity

We measured the therapeutic efficacy of entacapone and representative entacapone derivatives in hypoxia-induced retinopathy zebrafish model (Cao et al., Hypoxia-induced retinopathy model in adult zebrafish. Nat Protoc 2010, 5 (12), 1903-10).

We measured the therapeutic effect of entacapone and several representative entacapone derivatives on hypoxia-induced retinopathy zebrafish model. The transgenic Tg (flila:EGFP) zebrafish were treated with cobalt chloride for 4 days to induce retinopathy. Zebrafish were treated with cobalt chloride and entacapone or derivative on serial concentrations of 5 μM, 15 μM and 50 μM for 4 days. As positive control, zebrafish were treated with cobalt chloride and 100 μL/mL eye-drops augentropfen stulln mono containing 0.3 μg/mL digitalin and 2 μg/mL esculin.

The eye blood vessel diameter in model group (22.40) was significantly larger than that in untreated group (17.08, p<0.001), the eye ball volume in model group was smaller than that in untreated control group, and the inner plexiform layer and outer plexiform layer in model group was thinner than that in untreated control group. As the positive control, eye-drops augentropfen stulln mono inhibited retinal angiogenesis and repaired the retina structure (Table 1).

Figure 2:
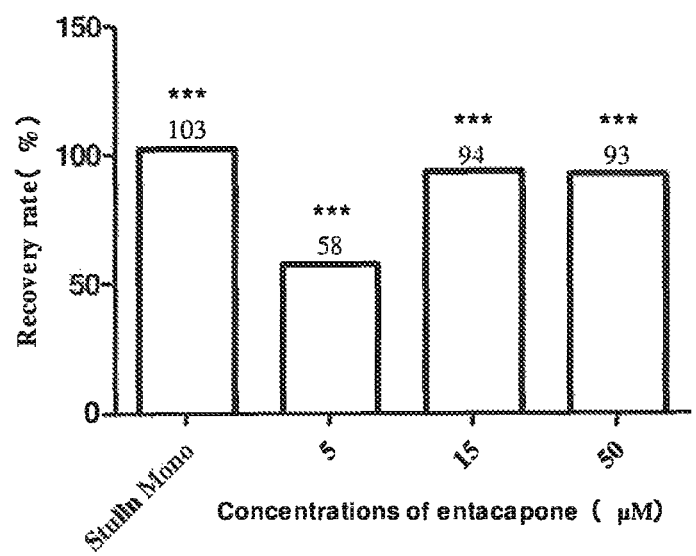
FIG. 2. The blood vessel diameter recovery rate. Values are presented as mean±SE (n=10). ***p<0.001, compared with the model group.

After treatment for 4 days, the retinal blood diameters were 19.33, 17.39 and 17.47 in zebrafish treated with entacapone on concentrations of 5 μM, 10 μM and 50 μM (p<0.001, compared with model group), and the blood vessel diameter recovery rate were 58%, 94% and 93%, respectively (FIG. 1). The eye ball volume was larger after entacapone treatment (FIG. 2). The inner plexiform layer and outer plexiform layer were thicker in entacapone-treated groups than that in model group. Results with representative entacapone derivatives were consistent, and indicate that entacapone and active derivatives thereof suppress hypoxia-induced retinal neoangiogenesis and improve histopathology of retinopathy.

TABLE 1

Entacapone inhibited retinal angiogenesis in zebrafish (n =10)

| Group | Concentration | Blood vessel diameter (mean ± SE) | Recovery rate (%) |
|---|---|---|---|
| Untreated control | — | 17.08 ± 0.51 | — |
| Model | — | 22.40 ± 0.44 | — |
| Stulln mono | digitalin 0.3 μg/mL, esculin 2 μg/mL | 16.90 ± 0.72*** | 103*** |
| Entacapone | 5 μM | 19.33 ± 0.52*** | 58*** |
|  | 15 μM | 17.39 ± 0.49*** | 94*** |
|  | 50 μM | 17.47 ± 0.29*** | 93*** |

***p < 0.001, as compared with model group, unit: pixel

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method for treating or inhibiting macular degeneration or age-related macular degeneration comprising administering a formulation comprising entacapone, an entacapone derivative or a stereoisomer, hydride, or pharmaceutically-acceptable salt thereof to a person in need thereof, wherein the formulation does not include an additional anti-Parkinson's medicament, a neuroactive agent, an anti- obesity active pharmaceutical ingredient, or an additional anti-diabetes active pharmaceutical ingredient, wherein the person does not have Parkinson's disease, obesity, diabetes or diabetic retinopathy, wherein the entacapone derivative is selected from the group consisting of:

a structure of formula Ia, a stereoisomer thereof, a hydride thereof, or a pharmaceutically-acceptable salt thereof:

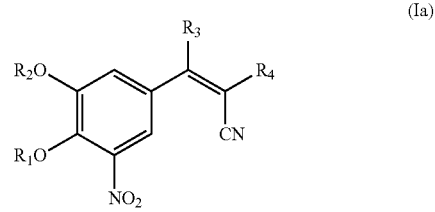

(Ia)

wherein:

$R_1$ and $R_2$ are independently H or Me;

$R_3$ is H, OH or NHR, wherein R is H or an optionally substituted, optionally hetero-, optionally cyclic $C_1$-$C_{18}$ hydrocarbyl; and $R_4$ is optionally substituted, optionally hetero-, optionally cyclic $C_1$-$C_{18}$ hydrocarbyl;

or a structure of formula Ib, a stereoisomer thereof, a hydride thereof, or a pharmaceutically-acceptable salt thereof:

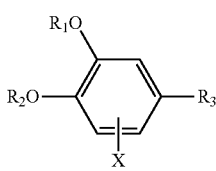

(Ib)

wherein R₁ and R₂ independently represent hydrogen, alkylcarbamoyl of 2 to 5 carbon atoms or alkylcarbonyl of 2 to 5 carbon atoms, X represents nitro or cyano and R₃ represents

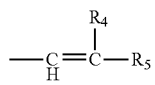

wherein R₄ represents cyano or alkylcarbonyl of 2 to 5 carbon atoms and R₅ represents cyano; alkylcarbonyl of 2 to 5 carbon atoms; or carbamoyl which is unsubstituted or substituted with alkyl of 1 to 8 carbon atoms, or hydroxyalkyl of 1 to 8 carbon atoms; or a structure of formula Ic, a stereoisomer thereof, a hydride thereof, or a pharmaceutically-acceptable salt thereof:

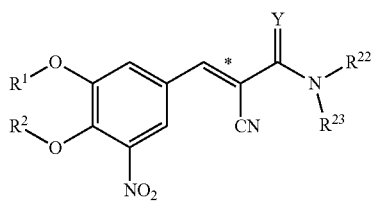

(Ic)

wherein
Y is sulfur or oxygen,
R¹ is a group of the following formula II

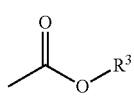

(II)

or when Y is S, R¹ can be in addition H,
R² is H or a group of formula II which may be the same as or different from R¹,
each R³ is independently (C₁-C₂₀)-alkyl, (CR⁴R⁵)x-R⁶, (C₁-C₂₀)-alkylene-(C₁-C₂₀)-alkoxy, (C₂-C₂₀)-alkenyl, (C₂-C₂₀)-alkynyl, (C₀-C₂₀)-alkylene- (C₃-C₁₈)-cycloalkyl, (C₀-C₂₀)-alkylene-(3-18-membered)-heterocycloalky 1, (C₁-C₂₀)-alkylene-(C₃-C₁₈)-cycloalkenyl, (C₀-C₂₀)- alkylene-(3-18-membered)-heterocycloalkenyl, (C₀-C₂₀)-alkylene- (C₆-C₁₈)-aryl, (C₀-C₂₀)-alkylene-(5-18-membered)-heteroaryl, (C₂-C₂₀)-alkenylene-(C₃-C₁₈)-cycloalkyl, (C₂-C₂₀)-alkenylene-(3-18-membered)-heterocycloalkyl, (C₂-C₂₀)-alkenylene-(C₃-C₁₈) -cycloalkenyl, (C₂-C₂₀)-alkenylene-(3-18-membered)- heterocycloalkenyl, (C₂-C₂₀) -alkenylene-(C₆-C₁₈)-aryl, or (C₂-C₂₀)- alkenylene-(5-18-membered)-heteroaryl, wherein the total number of carbon atoms of R³ is at most 30, each of R⁴ and R⁵ are independently of one another selected from the group consisting of H, (C₁-C₂₀)-alkyl, (C₁-C₂₀)-alkylene-hydroxy, (C₀-C₂₀)-alkylene-(C₁-C₂₀)-alkoxy, OH, (C₀-C₂₀)-alkylene-N(R⁷)CO-(C₁-C₂₀)-alkyl, (C₀-C₂₀)-alkylene-CON(R⁸)(R⁹), (C₀-C₂₀) -alkylene-COO-(C₁-C₂₀)-alkyl, (C₀-C₂₀)-alkylene-N(R¹⁰)(R¹¹), SO₃R¹⁷, (C₀-C₂₀)-alkylene -(C₆-C₁₈)-aryl, and (C₀-C₂₀)-alkylene-(5-18-membered)-heteroaryl, or R⁴ and R⁵ of the same group (CR⁴R⁵) or R⁴ and R⁵ of different groups (CR⁴R⁵) may form together a carbocyclic or heterocyclic ring having from 3 to 6 atoms, additionally, one or more non adjacent groups (CR⁴R⁵) may be replaced by O, CO, OCO, COO, CON(R¹⁹), N(R²⁰)CO, or NR²¹, R⁶ is independently H, (C₁-C₂₀)-alkyl, (C₂-C₂₀)-alkenyl, (C₂-C₂₀)- alkynyl, OH, O-(C₁-C₈) -alkyl, O-(C₀-C₈)-alkylene-(C₆-C₁₄)-aryl, CO-O-(C₁-C₈)-alkyl, CO-N(R¹²)(R¹³), N(R¹⁴)CO-(C₁-C₈)-alkyl, N(R¹⁵)(R¹⁶), SO₃R¹⁸, (C₀-C₂₀)-alkylene-(5-18-membered) -heteroaryl, or (C₀-C₂₀)-alkylene-(C₆-C₁₈)-aryl, R⁷, R¹⁴, R¹⁷, R¹⁸, R¹⁹, R²⁰, R²¹ are independently of one another H, or (C₁-C₂₀)-alkyl, R⁸, R⁹, R¹⁰, R¹¹, R¹², R¹³, R¹⁴, R¹⁵, R¹⁶ are independently of one another H, or (C₁-C₂₀) -alkyl, R²² and R²³ are independently selected from the group consisting of H and (C₁-C₁₅) -alkyl, and x is 1 to 14, wherein the alkyl, alkenyl, alkynyl, cycloalkyl, heterocycloalkyl, cycloalkenyl, heterocycloalkenyl, alkoxy, aryl, heteroaryl, alkenylene and alkylene groups may be unsubstituted or further substituted.

2. The method of claim 1, further comprising the step of detecting a resultant inhibition of macular degeneration.

3. The method of claim 1, wherein the person in need is at risk for developing macular degeneration or age-related macular degeneration, and the formulation is administered to that person in an amount effective to inhibit the development of macular degeneration or age-related macular degeneration.

4. The method of claim 1, wherein the person in need is afflicted with macular degeneration or age-related macular degeneration, and the formulation is administered to that person in an amount effective to treat macular degeneration or age-related macular degeneration.

* * * * *